(12) United States Patent
Lee et al.

(10) Patent No.: US 10,746,651 B2
(45) Date of Patent: Aug. 18, 2020

(54) OPTICAL METHOD FOR PREDICTING TREATMENT RESPONSE, SURVIVAL AND RECURRENCE OF ESOPHAGEAL CANCER PATIENTS

(71) Applicant: NATIONAL TAIWAN UNIVERSITY, Taipei (TW)

(72) Inventors: Jang-Ming Lee, Taipei (TW); I-Jen Hsu, Taipei (TW); Max Ti-Kuang Hou, Taipei (TW); Pei-Wen Yang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 281 days.

(21) Appl. No.: 15/703,941

(22) Filed: Sep. 13, 2017

(65) Prior Publication Data

US 2019/0017925 A1    Jan. 17, 2019

(30) Foreign Application Priority Data

Jul. 12, 2017 (TW) .............................. 106123380 A

(51) Int. Cl.
| | | |
|---|---|---|
| *G01N 33/48* | (2006.01) |
| *G01N 21/31* | (2006.01) |
| *G06F 19/00* | (2018.01) |
| *G01N 33/574* | (2006.01) |
| *G16H 20/40* | (2018.01) |
| *G16H 50/30* | (2018.01) |
| *G16H 20/10* | (2018.01) |
| *G16H 50/70* | (2018.01) |
| *G06G 7/58* | (2006.01) |
| *G01N 21/17* | (2006.01) |

(52) U.S. Cl.
CPC ........... *G01N 21/31* (2013.01); *G01N 33/574* (2013.01); *G06F 19/34* (2013.01); *G16H 20/10* (2018.01); *G16H 20/40* (2018.01); *G16H 50/30* (2018.01); *G16H 50/70* (2018.01); *G01N 2021/1742* (2013.01); *G01N 2201/1293* (2013.01); *G01N 2800/52* (2013.01)

(58) Field of Classification Search
None
See application file for complete search history.

(56) References Cited

PUBLICATIONS

Pei-Wen Yang et al., "Visible-absorption spectroscopy as a biomarker to predict treatment response and prognosis of surgically resected esophageal cancer", Scientific Reports, Published: Sep. 14, 2016.

*Primary Examiner* — Eric S DeJong
(74) *Attorney, Agent, or Firm* — WPAT, PC

(57) ABSTRACT

The present invention provides an optical method for predicting treatment response, survival and recurrence of esophageal cancer patients, comprising analyzing the spectral signatures of patient's tumor tissue spectra. By the features of the present invention, the prediction result achieves the sensitivity of 75% and specificity of 73.3% in concurrent chemoradiotherapy (CCRT) response; the survival prediction rate achieves the sensitivity of 100%; the recurrence prediction rate achieves the sensitivity of 85.7%.

20 Claims, 11 Drawing Sheets

OPTICAL METHOD FOR PREDICTING TREATMENT RESPONSE, SURVIVAL AND RECURRENCE OF ESOPHAGEAL CANCER PATIENTS

CROSS-REFERENCE TO RELATED APPLICATION

This application claims the priority of Taiwanese patent application No. 106123380, filed on Jul. 12, 2017, which is incorporated herewith by reference.

BACKGROUND OF THE INVENTION

1. Field of the Invention

The present invention relates to a method for predicting treatment response, survival and recurrence of esophageal cancer patients, more specifically, the present invention relates to a method for predicting treatment response, survival and recurrence of esophageal cancer patients using visible optical absorption spectra.

2. The Prior Arts

Esophageal cancer is a deadly disease with high risk of local recurrence and distant metastasis even among patients with early stage tumors. Primary esophageal cancer presents most often as esophageal squamous cell carcinoma (ESCC) or adenocarcinoma (EADC). The standard treatment for locally advanced esophageal cancer is neoadjuvant (preoperative) concurrent chemoradiotherapy (CCRT) with or without surgery. Patients with ESCC can enjoy better survival once they have shown a good response to CCRT. The pathologically complete remission rate has only ranged from 10% to 40% under different treated protocols. Prognosis of esophageal cancer is still poor with a 5-year survival rate of less than 20% even with multiple treatment modalities. More than 50% of the patients encounter local-regional recurrence or distant metastases within 2 to 3 years. The TNM staging has been considered the gold standard in predicting clinical outcome and guiding treatment strategy. However, some patients even with early stage disease experience local or systemic failure early after treatment. Therefore, an effort is underway to identify and make use of multiple reliable prognostic markers to improve management of patients with esophageal cancer.

Cancer formation is usually triggered by accumulating genetic or epigenetic mutations, which result in great changes in the biochemical compounds in cells. Different degrees of malignancy are accompanied by different molecular compounds in individual cancer cells, which in turn call for different therapeutic strategies. Current technologies, such as microarrays, are widely used to analyze global differences in biological materials between individual samples. These analytic platforms provide detailed information about global changes in gene expression; however, they are not designed for real-time in-situ assessment and require considerable time and cost.

As described above, esophageal cancer is a deadly disease with high risk of recurrence. The median survival after recurrence of ESCC is reportedly only about 8 months. Therefore, it is an effort for a researcher in related arts to developing a method can be measured in-situ and can predict CCRT response and prognosis.

SUMMARY OF THE INVENTION

To solve the problems described above, the present invention provides an optical method for predicting treatment response of esophageal cancer patients, comprising: obtaining an optical absorption spectrum of a tumor tissue sample from an esophageal cancer patient, the optical absorption spectrum of the tumor tissue sample is a visible optical absorption spectrum; normalizing the optical absorption spectrum of the tumor tissue sample, incorporating into a pre-stored database and grouping by a principal component analysis; wherein a plural of spectral variables of principal component analysis are obtained from wavelength of 450-475 nm and 625-650 nm; and grouping all the spectra by PC_7 and PC_2 value of principal component analysis to determine the esophageal cancer patient is identified as having good response or poor response to the treatment; wherein the treatment is concurrent chemoradiotherapy.

In one embodiment of the present invention, the optical absorption spectrum of the tumor tissue sample is an optical absorption spectrum captured by a wavelength from 450 to 650 nm.

In one embodiment of the present invention, the optical absorption spectrum of the tumor tissue sample is a transmission absorption spectrum.

In one embodiment of the present invention, the pre-stored database is pre-stored an effective amount of normalized optical absorption spectra of tumor tissue samples.

The present invention also provides an optical method for predicting survival of esophageal cancer patients, comprising: obtaining an optical absorption spectrum of a tumor tissue sample from an esophageal cancer patient, the optical absorption spectrum of the tumor tissue sample is a visible optical absorption spectrum; normalizing the optical absorption spectrum of the tumor tissue sample, incorporating into a pre-stored database and grouping by a principal component analysis; wherein a plural of spectral variables of principal component analysis are obtained from wavelength of 450-475 nm and 625-650 nm; and grouping all the spectra by PC_1 and PC_3 value of principal component analysis to determine the esophageal cancer patient is identified as poor survival or non-poor survival.

In the method described above, the poor survival defined as the esophageal cancer patient is alive within 1 year and the non-poor survival defined as the esophageal cancer patient is alive over 1 year.

In one embodiment of the present invention, the optical absorption spectrum of the tumor tissue sample is an optical absorption spectrum captured by a wavelength from 450 to 650 nm.

In one embodiment of the present invention, the optical absorption spectrum of the tumor tissue sample is a transmission absorption spectrum.

In one embodiment of the present invention, the pre-stored database is pre-stored an effective amount of normalized optical absorption spectra of tumor tissue samples.

The present invention also provides an optical method for predicting recurrence of esophageal cancer patients, comprising: obtaining an optical absorption spectrum of a tumor tissue sample from an esophageal cancer patient, the optical absorption spectrum of the tumor tissue sample is a visible optical absorption spectrum; normalizing the optical absorption spectrum of the tumor tissue sample, incorporating into a pre-stored database and grouping by a principal component analysis; wherein a plural of spectral variables of principal component analysis are obtained from wavelength of 450-475 nm and 625-650 nm; and grouping all the spectra by PC_6 and PC_5 value of principal component analysis to determine the esophageal cancer patient is identified as recurrence or no recurrence.

In the method described above, the recurrence defined as the esophageal cancer patient experience tumor recurrence or die within 6 months and the no recurrence defined as the esophageal cancer patient wouldn't experience tumor recurrence within 6 months.

In one embodiment of the present invention, the optical absorption spectrum of the tumor tissue sample is an optical absorption spectrum captured by a wavelength from 450 to 650 nm.

In one embodiment of the present invention, the optical absorption spectrum of the tumor tissue sample is a transmission absorption spectrum.

In one embodiment of the present invention, the pre-stored database is pre-stored an effective amount of normalized optical absorption spectra of tumor tissue samples.

By the features of the present invention, the present invention demonstrates the visible-absorption spectroscopy as a tool for evaluating CCRT response and as a prognostic biomarker of esophageal cancer. Visible light is safe and easy to work with for clinical diagnosis. Further, the CCRT response prediction result achieves the sensitivity of 75% and specificity of 73.3%; the survival prediction rate achieves the sensitivity of 100%; the recurrence prediction rate achieves the sensitivity of 85.7%.

The preferred embodiments described below are disclosed for illustrative purpose but to limit the modifications and variations of the present invention. Thus, any modifications and variations made without departing from the spirit and scope of the invention should still be covered by the scope of this invention as disclosed in the accompanying claims.

DETAILED DESCRIPTION OF THE PREFERRED EMBODIMENT

Figure 1:
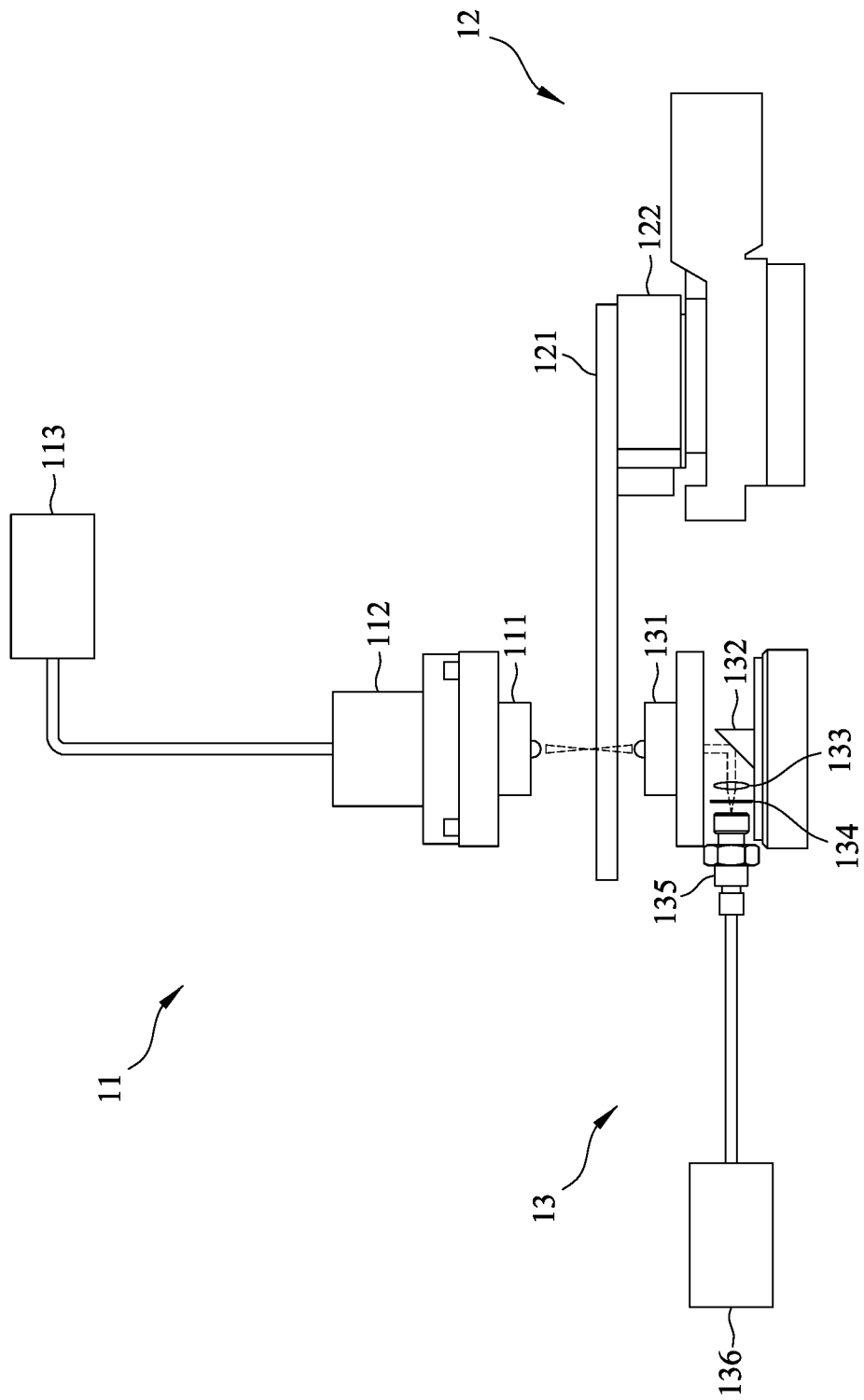
FIG. 1 shows the optical system of the present invention for measuring transmission absorption spectra.

The present invention provides an optical method for predicting treatment response of esophageal cancer patients, comprising: obtaining an optical absorption spectrum of a tumor tissue sample from an esophageal cancer patient, the optical absorption spectrum of the tumor tissue sample is a visible optical absorption spectrum; normalizing the optical absorption spectrum of the tumor tissue sample, incorporating into a pre-stored database and grouping by a principal component analysis; wherein a plural of spectral variables of principal component analysis are obtained from wavelength of 450-475 nm and 625-650 nm; and grouping all the spectra by PC_7 and PC_2 value of principal component analysis to determine the esophageal cancer patient is identified as having good response or poor response to the treatment; wherein the treatment is concurrent chemoradiotherapy (CCRT).

The pre-stored database pre-stored an effective amount of normalized optical absorption spectra of tumor tissues. In an embodiment of the present invention, the pre-stored database incorporates an effective amount of normalized optical absorption spectra of tumor tissues from at least 50 patients. The tumor tissue can be a fresh sample or a frozen sample. The tumor tissue is preferably a fresh sample.

The present invention also provides an optical method for predicting survival of esophageal cancer patients, comprising: obtaining an optical absorption spectrum of a tumor tissue sample from an esophageal cancer patient, the optical absorption spectrum of the tumor tissue sample is a visible optical absorption spectrum; normalizing the optical absorption spectrum of the tumor tissue sample, incorporating into a pre-stored database and grouping by a principal component analysis; wherein a plural of spectral variables of principal component analysis are obtained from wavelength of 450-475 nm and 625-650 nm; and grouping all the spectra by PC_1 and PC_3 value of principal component analysis to determine the esophageal cancer patient is identified as poor survival or non-poor survival.

In the method described above, the poor survival defined as the esophageal cancer patient is alive within 1 year and the non-poor survival defined as the esophageal cancer patient is alive over 1 year.

The present invention also provides an optical method for predicting recurrence of esophageal cancer patients, comprising: obtaining an optical absorption spectrum of a tumor tissue sample from an esophageal cancer patient, the optical absorption spectrum of the tumor tissue sample is a visible optical absorption spectrum; normalizing the optical absorption spectrum of the tumor tissue sample, incorporating into a pre-stored database and grouping by a principal component analysis; wherein a plural of spectral variables of principal component analysis are obtained from wavelength of 450-475 nm and 625-650 nm; and grouping all the spectra by PC_6 and PC_5 value of principal component analysis to determine the esophageal cancer patient is identified as recurrence or no recurrence.

In the method described above, the recurrence defined as the esophageal cancer patient experience tumor recurrence or die within 6 months and the no recurrence defined as the esophageal cancer patient wouldn't experience tumor recurrence within 6 months.

In one embodiment of the present invention, the optical absorption spectrum of a tumor tissue sample is an optical absorption spectrum captured by a wavelength from 450 to 650 nm.

As used herein, "approximately" shall generally mean within 20 percent, preferably within 10 percent, and more preferably within 5 percent of a given value or range. Numerical quantities given herein may vary depending on the different instruments or different measurement methods. Thus, numerical quantities given herein are approximate, meaning that the term "approximately" can be inferred if not expressly stated.

We describe the present invention by the embodiments below.

Embodiment 1 Study Population and Tissue Collection

A total of 120 patients treated with surgical resection for primary esophageal cancer at National Taiwan University Hospital (NTUH) from 2011 to 2013 were enrolled in the study. The characteristics of the 120 enrolled patients are listed by fresh (n=56) or frozen (n=64) analysis in Table 1. Tissue sets, including tumorous and non-tumorous (normal, distant from the tumor) samples of esophageal tissue, were collected during surgical dissection. Of these specimens, 56 sets were fresh tissues analyzed to determine their optical spectrum within 1 hour after tissue dissection. The remaining 64 sets were frozen tissues which were stored in a −80° C. freezer and analyzed within 1 year. Patients were followed up in our outpatient clinics. Information about patients, including demographics, histology, TNM stage, treatment response, survival and recurrence, was obtained by medical chart review. This study was approved the Research Ethics Committee of NTUH (No. 201101065RB). Written informed consent was obtained from all participating subjects. All the study methods were carried out in accordance with the approved guidelines.

TABLE 1

Characteristics of patients.

|  | N | Fresh | Frozen |
|---|---|---|---|
| Frozen |  | 56 (46.7) | 64 (53.3) |
| ESCC | 113 | (94.2) | 52 (92.9) | 61 (95.3) |
| EADC | 5 | (4.2) | 4 (7.1) | 1 (1.6) |
| others | 2 | (1.7) | 0 (0) | 2 (3.1) |
| Gender |
| Female | 8 | (6.7) | 3 (5.4) | 5 (7.8) |
| Male | 112 | (93.3) | 53 (94.6) | 59 (92.2) |
| Age |  |  | 57.95 ± 8.74 | 56.14 ± 10.01 |
| T-stage |
| 0 | 35 | (29.2) | 15 (26.8) | 20 (31.3) |
| 1 | 33 | (27.5) | 11 (19.6) | 22 (34.4) |
| 2 | 24 | (20.0) | 13 (23.2) | 11 (17.2) |
| 3 | 28 | (23.3) | 17 (30.4) | 11 (17.2) |
| N-stage |
| 0 | 82 | (68.3) | 36 (64.3) | 46 (71.9) |
| 1 | 29 | (24.2) | 17 (30.4) | 12 (18.8) |
| 2 | 4 | (6.3) | 3 (5.4) | 4 (6.3) |
| 3 | 2 | (3.1) | 0 (0) | 2 (3.1) |
| Site |
| upper | 28 | (23.3) | 13 (23.2) | 15 (23.4) |
| middle | 44 | (36.7) | 16 (28.6) | 28 (43.8) |
| lower | 48 | (40.0) | 27 (48.2) | 21 (32.8) |
| CCRT |
| CCRT | 17 | (14.2) | 7 (12.5) | 10 (15.6) |
| no CCRT | 103 | (85.8) | 49 (87.5) | 54 (84.4) |
| CCRT response |
| Complete remission | 40 | (38.8) | 15 (30.6) | 25 (46.3) |
| Microscopic tumor | 30 | (29.1) | 18 (36.7) | 12 (22.2) |
| Macroscopic tumor | 33 | (32.0) | 16 (32.7) | 17 (31.5) |

ESCC, esophageal squamous cell carcinoma.
EADC, esophageal adenocarcinoma.
CCRT, concurrent chemoradiotherapy.

Of these patients, 93.3% (n=112) were male, 94.2% (n=113) were with ESCC, and 68.3% (n=82) were without lymph node metastasis. The location of tumors in the upper, middle and lower third of the esophagus were 28 (23.3%), 44 (36.7%) and 48 (40.0%) respectively. There were 103 (85.8%) patients treated with CCRT [CCRT (+)] of which 40 (38.8%) had complete remission.

Embodiment 2 Measurement and Analysis

Embodiment 2-1 Two Dimensional Absorption Spectrum Measurement System (TDAS) and Spectral Analysis One embodiment of the present invention, an optical system for measurement of the transmission absorption spectrum was designed and built as shown in FIG. 1. The system is assembled with three components: one is a illumination unit 11, another is a positioning unit 12 and the other is a detection unit 13. The illumination unit 11 comprises an achromatic focusing lens 111 and a collimating lens 112 coupled with an optical fiber attached to a tungsten halogen light source 113 (Ocean Optics, HL2000-HP-FHSA) with a wavelength range from 360 nm to 1700 nm and an output power of 20 W. The positioning unit 12 comprises a sample stage 121 attached to a two-dimensional translation stage 122 (SIGMA KOKI, SGSP15-10XY) for positioning and scanning the sample. The detection unit 13 comprises a collecting lens 131, a reflection prism 132 and a collimating lens 133 coupled to a spectrometer 136 (Ocean Optics, USB2000) via an optical fiber 135 after passing through a neutral-density filter 134. The main structure of the system is made of polymethyl methacrylate and the whole system is automatically controlled and synchronized with a computer program. The sample stage 121 is moved by the computer-controlled two-dimensional translation stage 122 to perform a two-dimensional scan of the sample to be examined. The light transmitted through the sample is collected by the collecting lens 131 and reflected by the reflection prism 132 at a right angle before being coupled to the optical fiber 135 with the collimating lens 133. The transmission spectrum is detected by the fiber-coupled spectrometer 136 which is automatically triggered by a computer where the signal is processed. The scanning range of each sample is 5 mm×5 mm with a step size of 500 μm. The absorbance at each point of the sample is given by $$A(\lambda) = \log \frac{I_0(\lambda)}{I(\lambda)}$$

wherein $I_0(\lambda)$ is the spectrum of the incident light and $I(\lambda)$ is the measured transmission spectrum. Because the measured spectra show more significant signals and differences in wavelength range between 450 nm and 650 nm, each absorbance is windowed in this wavelength range and is intensity-shifted so that the minimum value is zero, in order to obtain the relative absorbance. The relative absorbance is then normalized so that the area under the spectrum curve is unity to obtain the normalized relative absorbance.

Embodiment 2-2 Data Analysis

The noise spectra, including glass-like spectra, heterogenesis spectra, and outlier signals, were removed using the R statistical package, and the resulting absorption spectra were quantile normalized using the limma package. Median values of both the non-tumor spectra (spectra of normal tissue)

and tumor spectra (spectra of tumor tissue) were analyzed. We obtain the median values of tumor or non-tumor tissue within each specific group (the most representative absorption intensity of each tissue type within each specific group), and the median spectra were constructed using Origin software (OriginLab, Northampton, Mass., USA) and compared by independent t-test. To further analyze the spectral signatures between groups, the spectral data were grouped by applying principal component analysis (PCA). The associations between spectral signatures and tumor development or CCRT response were described by odds ratios (ORs) obtained from logistic regression. Hazard ratios (HRs) of death and disease recurrence obtained by multivariate Cox regression analysis were used in analyzing the correlation between spectral features and prognosis, including survival and disease recurrence in patients. Crude correlations between spectral groups and survival or disease recurrence were estimated by the Kaplan-Meier method and log-rank test. In the present specification, patients with a complete pathological response or microscopic residual disease after CCRT were classified as "good responders" to CCRT, whereas those with macroscopic residual disease or progressive disease after treatment were classified as "poor responders" to CCRT. Those who were alive over 1-year (12 months) after surgery were considered as having "non-poor survival" whereas patients who died within 1 year after surgery were defined as having "poor survival"; "Recurrence" was defined as patients who died or had detectable tumor recurrence within 6 months. Patients who were recurrence-free over 6 months after surgery were placed in the "no recurrence" group. Overall survival (OS) was defined as the time interval from surgical removal of esophageal tumor (esophagectomy) to the last follow-up or death from disease. Progression-free survival (PFS) was defined as the time elapsed between esophagectomy and death or detection of disease recurrence, including local recurrence or distant metastasis, of the tumor. The statistical analyses were performed by SPSS 16.0 (SPSS Inc., Chicago, Ill., USA). A p-value less than 0.05 was reported as statistically significant.

Embodiment 3 Median Absorption Spectra of CCRT (−)Esophageal Tissues

Figures 2A, 2B:
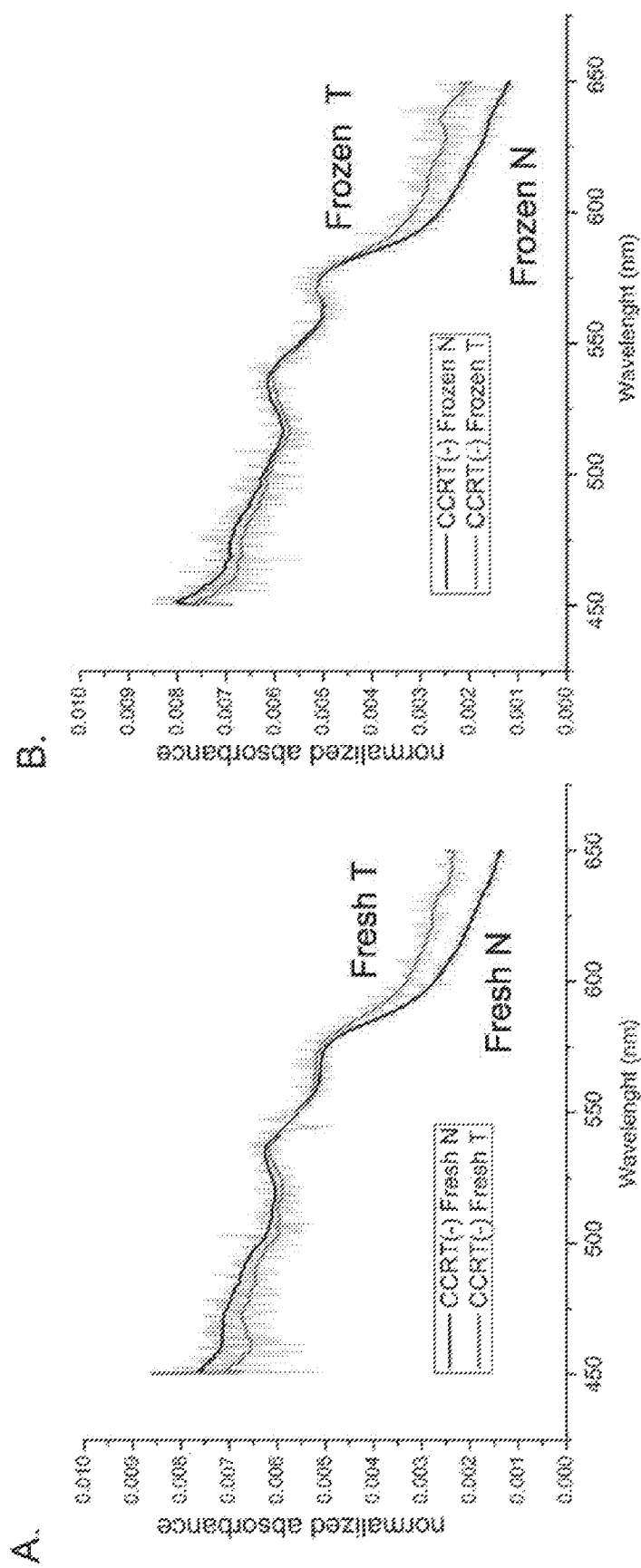
FIGS. 2A-F show the median absorption spectra of fresh tissue (2A, 2C, 2E, 2F), frozen tissue (2B, 2D) tissue without CCRT treatment (2A-D) or tissue with CCRT treatment (2E, 2F); Tissue from early-stage patients (2C, 2D); Tumor tissue from poor responders (2E) or good responders (2F) to CCRT. N, normal; T, tumor.
Figures 2C, 2D:
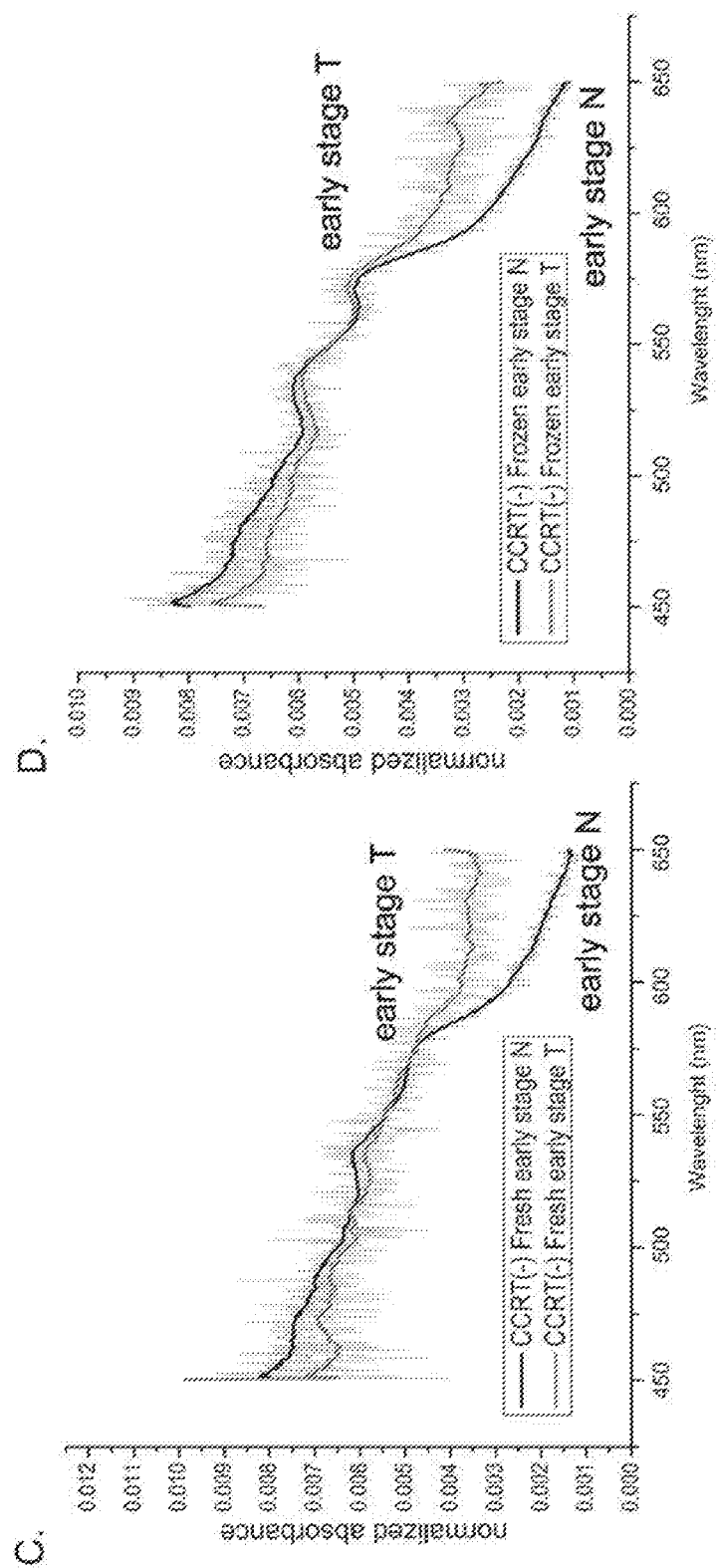
Figures 2E, 2F:
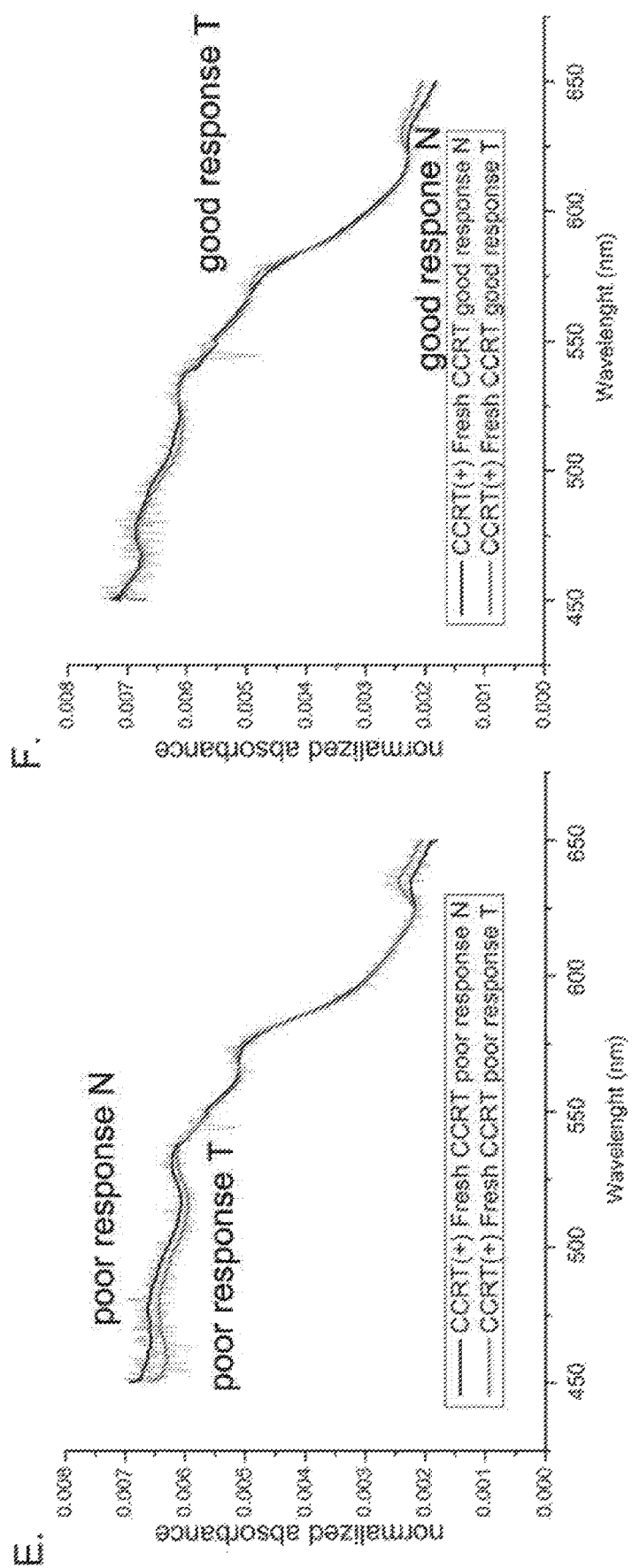

Median absorption spectra of normal and malignant tissue specimens from patients treated without CCRT (CCRT(−)) and analyzed by TDAS freshly are presented in FIG. 2A. The spectra of the malignant tissue showed lower absorption in short-wavelengths (around 450-500 nm) and higher absorption in long-wavelengths (around 575-650 nm) compared with the median spectra of normal tissue. Similar results were observed in the frozen tissue (FIG. 2B). These features were also evident in the tissue specimens from patients with early tumor stage (FIGS. 2C,D). Interestingly, the freshly analyzed tumor tissue from poor responders to CCRT also displayed lower absorption in short wavelengths (around 450-500 nm) and higher absorption in long wavelengths (around 625-650 nm) in comparison with the spectrum of CCRT-treated normal tissue (FIG. 2E). These features were less obvious in tissue from good responders (FIG. 2F).

Embodiment 4 Median Absorption Spectra of CCRT (+) Esophageal Tissues

Figures 3A, 3B:
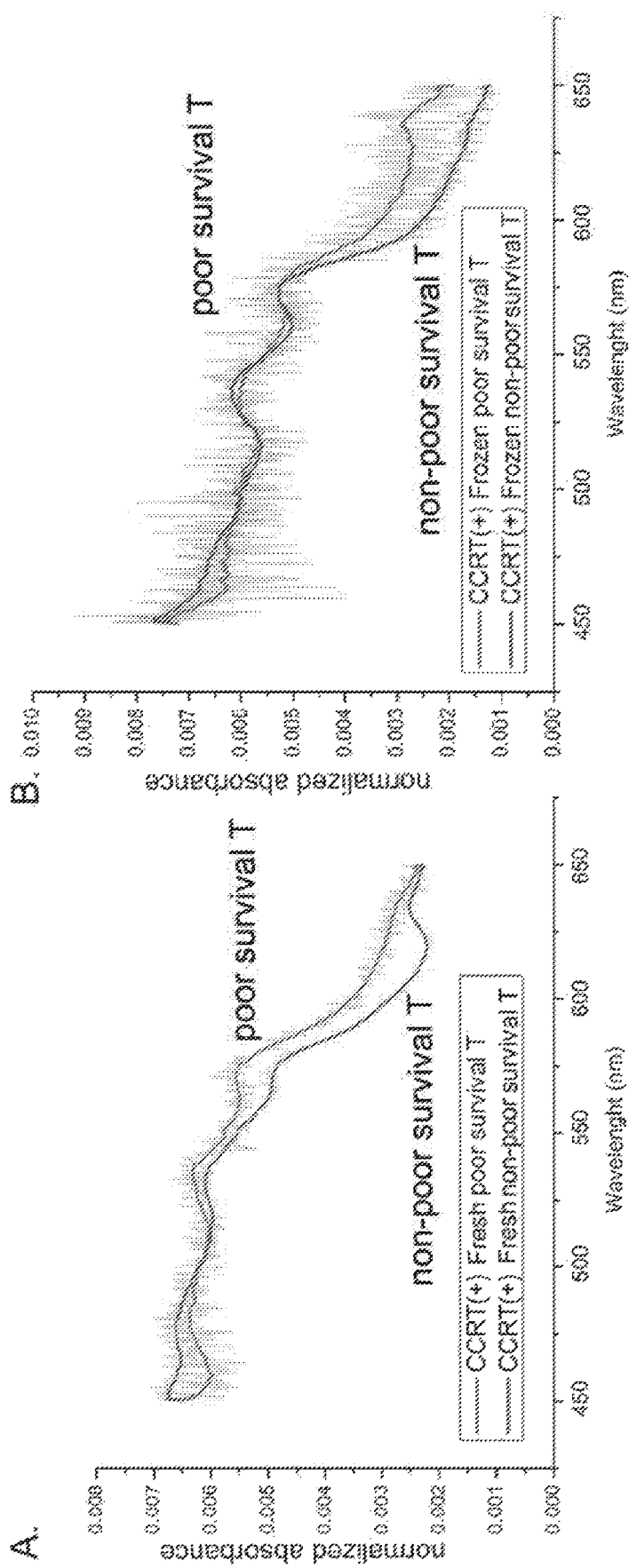
FIGS. 3A-D show the median absorption spectra of fresh (3A, 3C) or frozen (3B, 3D) tissue samples treated with CCRT; Tissues from non-poor or poor survival groups (3A, 3B); Tissues from recurrence or no recurrence groups (3C, 3D); T, tumor.
Figures 3C, 3D:
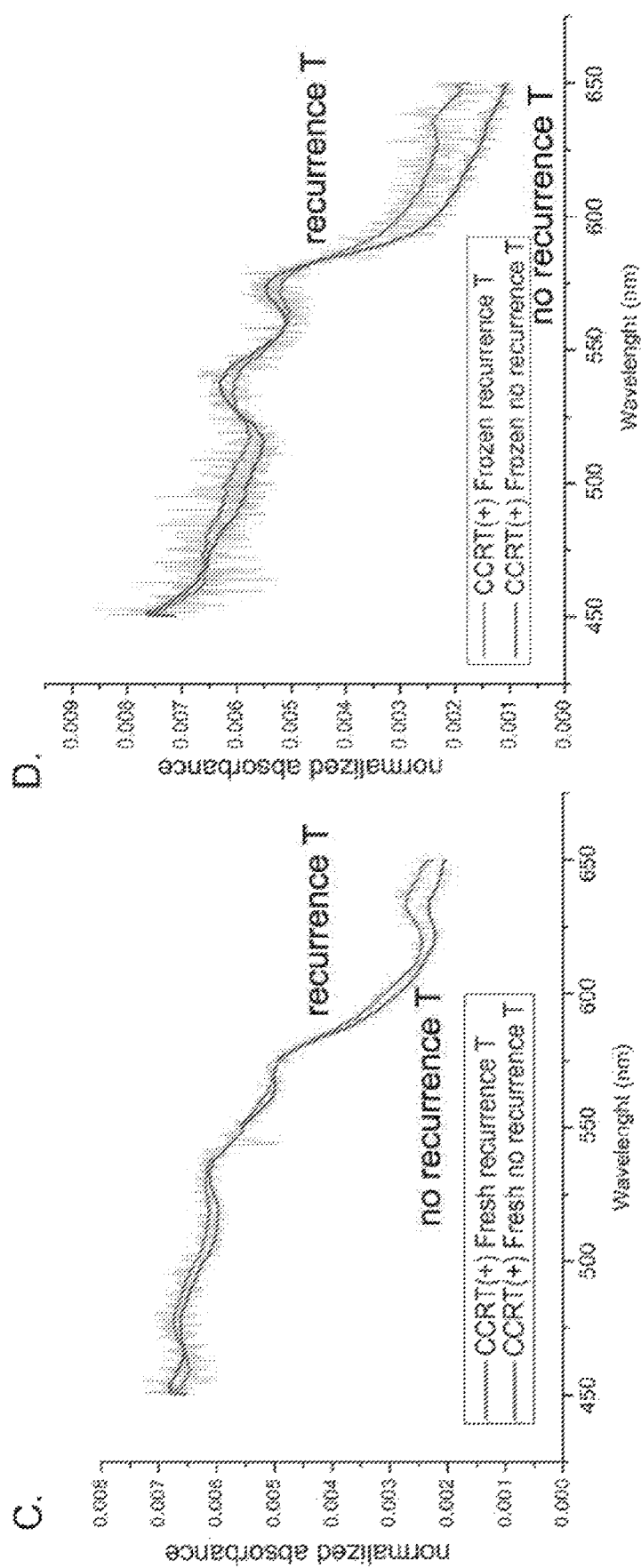

The median spectral signatures of tumor tissue also displayed notable differences between non-poor survival and poor survival groups. In the fresh CCRT (+) tumor tissue samples, the median spectra of patients with poor survival also showed reduced absorption in short wavelengths (around 450-500 nm) and enhanced absorption in long wavelengths (around 500-650 nm) compared with the spectra of the non-poor survival group (FIG. 3A). Similar results were obtained in the frozen tissues (FIG. 3B). Spectral analysis of fresh tumor also showed higher absorption in long wavelengths (around 600-650 nm) among the recurrence group compared with the no-recurrence group (FIG. 3C). Parallel analysis of frozen tissue revealed a similar result (FIG. 3D).

Embodiment 5 Classification of Esophageal Tissue Spectra by PCA

We further analyzed the spectral signatures by principal component analysis (PCA). Because we hope to establish a prediction model for fresh sample analysis, we enrolled all the fresh samples (n=56) for the PCA analysis. We also included CCRT (−) frozen samples (n=10) in the PCA analysis due to the limited fresh samples of CCRT (−) tissues (n=7). There were a total of 66 cases included for PCA. The total spectral data consist of 132 sets, 66 of normal tissue spectra and 66 of tumor tissue spectra. There were 900 intensity values in the raw data of each spectrum in the wavelength range of 450-650 nm which were defined as the spectral variables. The wavelengths of 450 to 475 nm and of 625 to 650 nm were found by independent t-test to clearly divide the patients into different groups, including normal and tumor groups, good response and poor response groups, non-poor survival and poor survival groups, and recurrence versus no recurrence groups. PCA thus extracted 150 spectral variables from the wavelengths of 450 to 475 nm and of 625 to 650 nm. The first eight PCs (principal components) were able to describe about 79% of the variation in the spectral data from all fresh samples and CCRT (−) frozen samples.

Embodiment 6 Spectral Signatures of Good Response and Poor Response to CCRT

Figure 4:
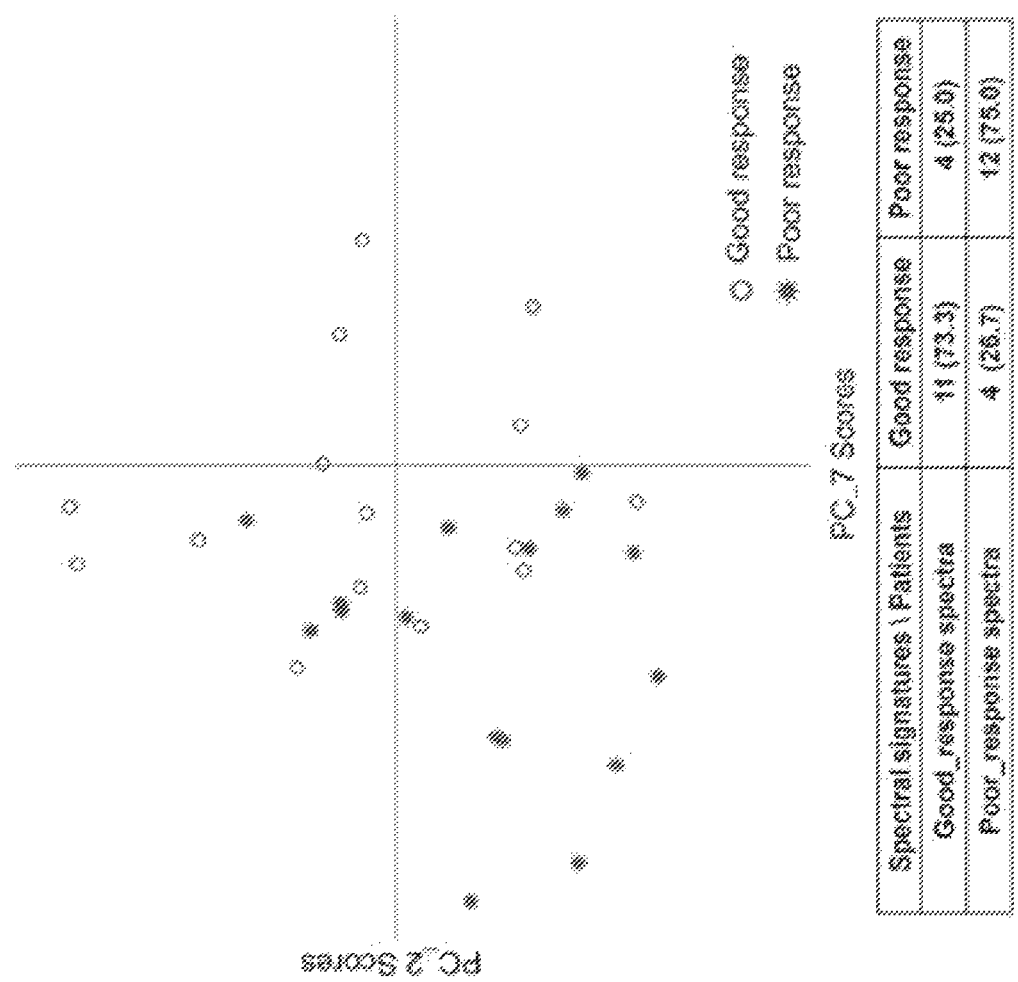
FIG. 4 shows the spectral signatures of CCRT (+) tissues, good-response spectra and poor-response spectra, classified by the scatter plots of PC_7 and PC_2 scores from PCA; PC, principal component; PCA, principal component analysis.

We then examined whether the absorption spectra could be used to evaluate CCRT response in esophageal cancer by including the 31 cases treated with CCRT for which a clear pathologic response record existed. It was found that the values of PC_7 and PC_2 could be used to differentiate poor responders and good responders with a sensitivity of 75% and a specificity of 73.3% (FIG. 4). Patients identified as having a poor-response spectra showed a significant, more than 11-fold increased risk of poor response compared with patients identified as having a good-response spectrum (Logistics regression model, OR [95% CI]=11.69 (1.73-79.20), P=0.012, Table 2).

TABLE 2

Association of spectra groups with tumor risk and CCRT response under multivariate analysis

|  | N | OR (95% CI) | *P value |
|---|---|---|---|
| CCRT response |  |  | 0.012 |
| Good_response spectra | 15 | 1 |  |
| Poor_response spectra | 16 | 11.69 (1.73-79.20) |  |

*Adjusted for cell type and site.

Figure 5A:
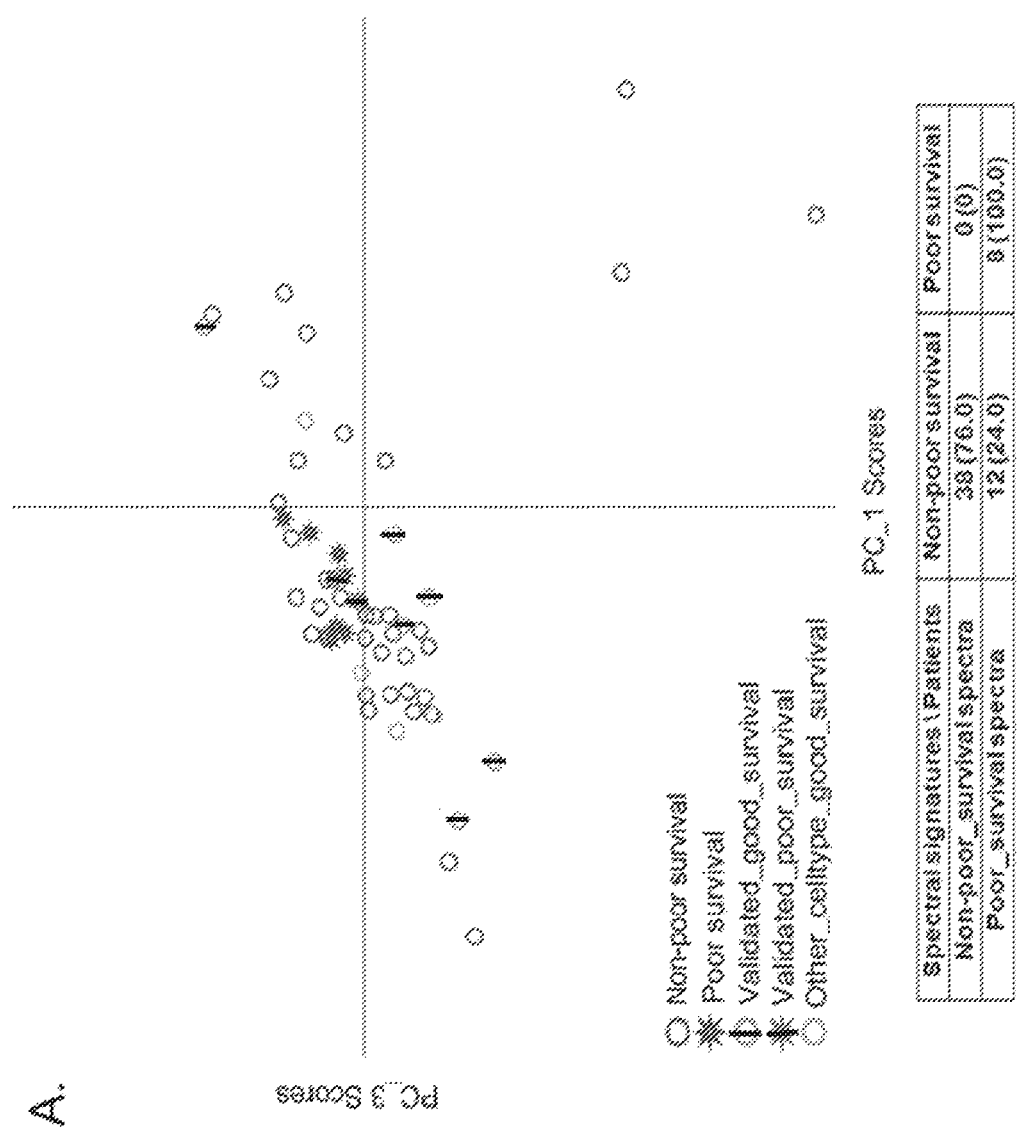
FIGS. 5A-B show the PCA of tumor tissue samples; (A) spectral signatures of non-poor-survival spectra and poor-survival spectra by the scatter plots of PC_1 and PC_3 scores and (B) spectral signatures of no-recurrence and recurrence spectra by the scatter plots of PC_6 and PC_5 scores.
Figure 5B:
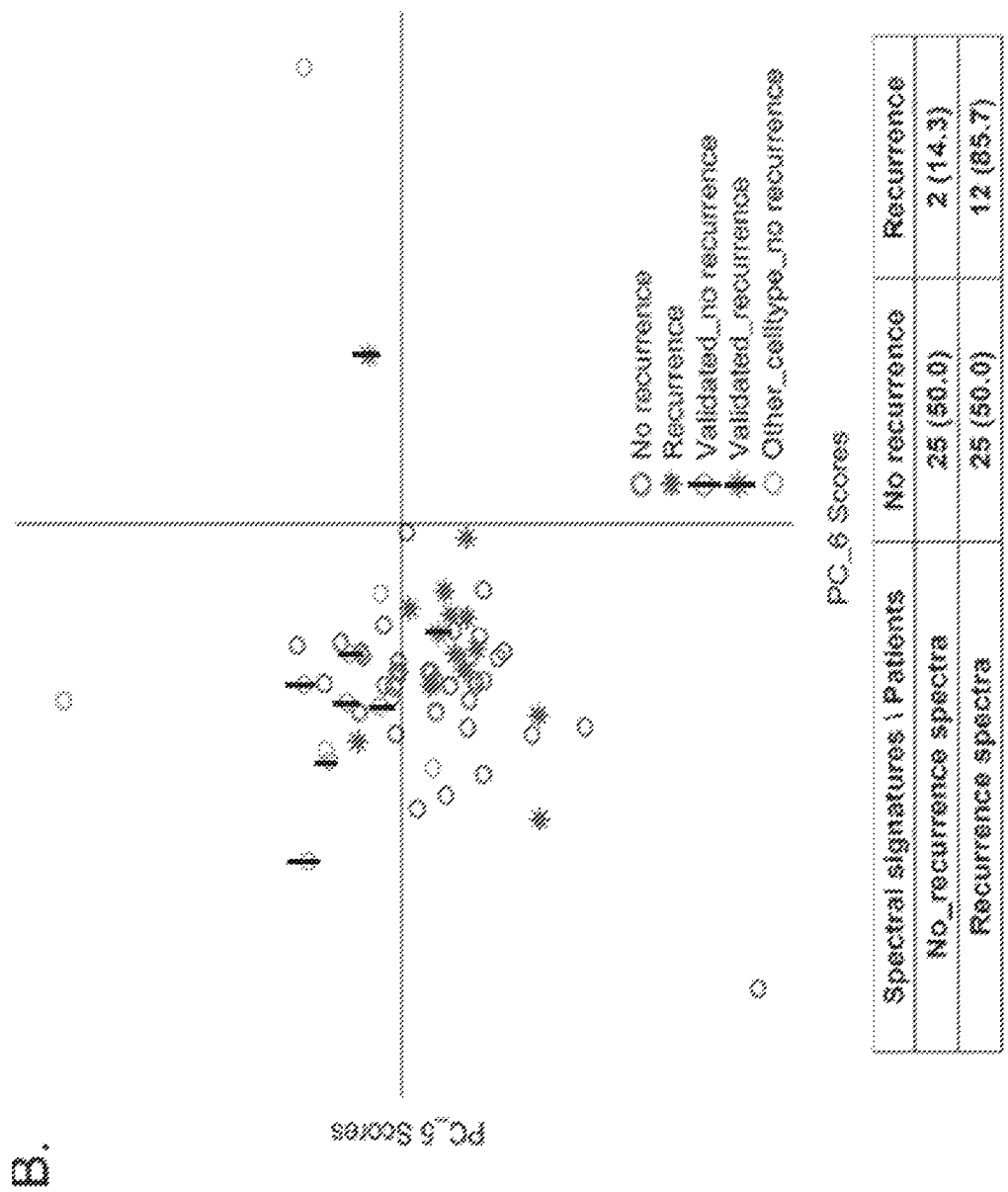

Embodiment 7 Optical Spectra Predict Overall Survival and Early Disease Recurrence of Esophageal Cancer We evaluated whether absorption spectroscopy data might serve as a biomarker to predict the prognosis of surgically resected esophageal cancer using PCA to analyze the cases with a follow up of more than 12 months (n=58 for survival analysis) or more than 6 months (n=64, for recurrence analysis). The median spectra from fresh ESCC tissue were assigned to a training data set. The scatter plot constructed by PC_1 and PC_3 scores perfectly separated the poor survival group from the non-poor survival group with a sensitivity of 100% (FIG. 5A). Frozen CCRT (−) ESCC samples (n=7, 6 non-poor survival and 1 poor survival) and tissue of other histological types (n=4, all non-poor survival) were assigned to a testing set for validation. The tissue from the patient with poor survival in the testing set was clustered with the poor survival group in the training set (FIG. 5A). 7 of the 9 patients in the testing set with non-poor survival displayed non-poor survival spectra and were classified properly (FIG. 5A). The specificity for survival prediction was 76% combing training and testing group. We then analyzed the association between spectral signature and early recurrence of patients. Patients who experienced tumor recurrence or died within 6 months after surgery were assigned to the recurrence group in this embodiment. The PC_6 and PC_5 scores efficiently separated the recurrence group from the no recurrence group in the training set (FIG. 5B). In the testing set, 2 patients had early recurrence and 11 were recurrence-free. One patient with early recurrence (50%) and 10 patients (91%) without early recurrence were classified correctly (FIG. 5B). Overall, the sensitivity and specificity for predicting recurrence were 85.7% and 50% respectively.

Figure 6A:
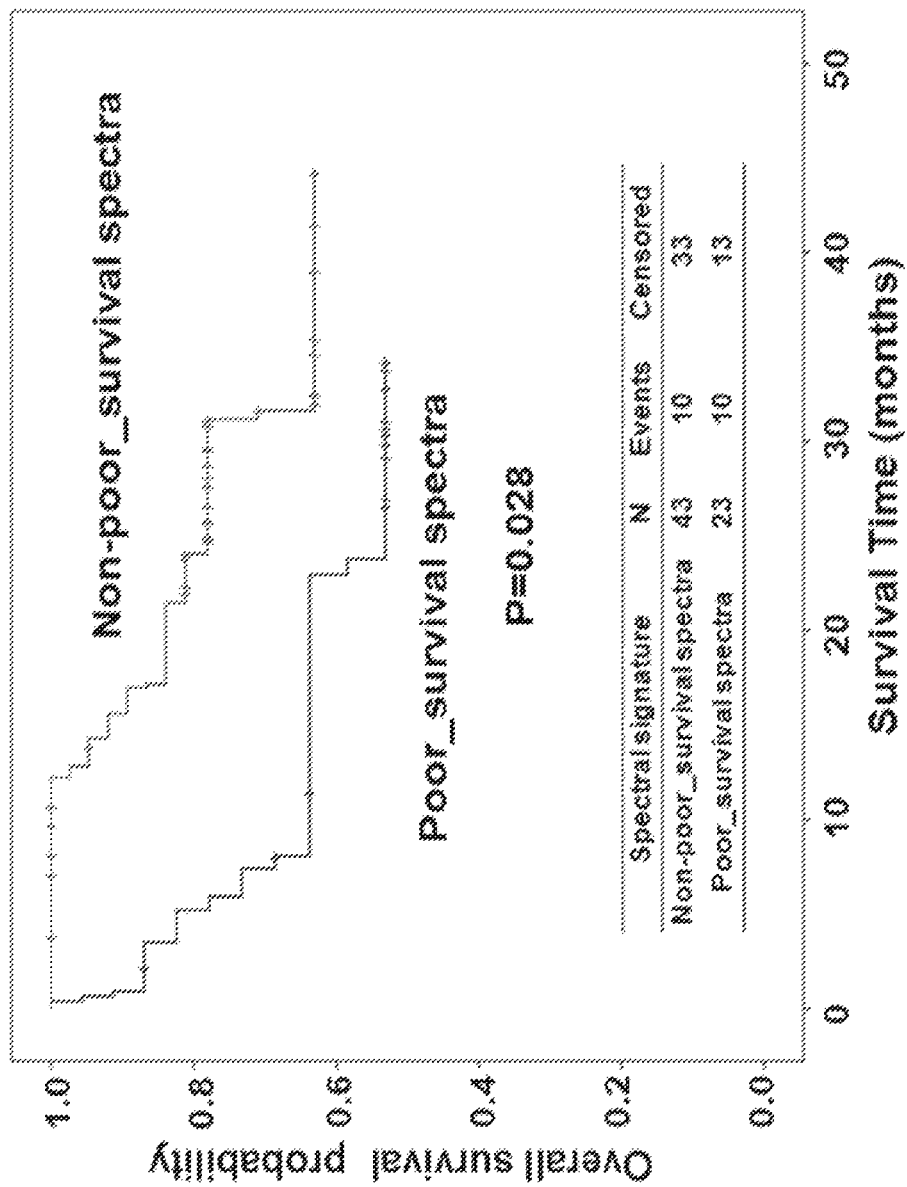
FIGS. 6A-B show the Kaplan-Meier estimates of overall survival by the spectral signatures of non-poor-survival spectra and poor-survival spectra (A), and progression-free survival by the spectral signatures of no-recurrence spectra and recurrence spectra (B).
Figure 6B:
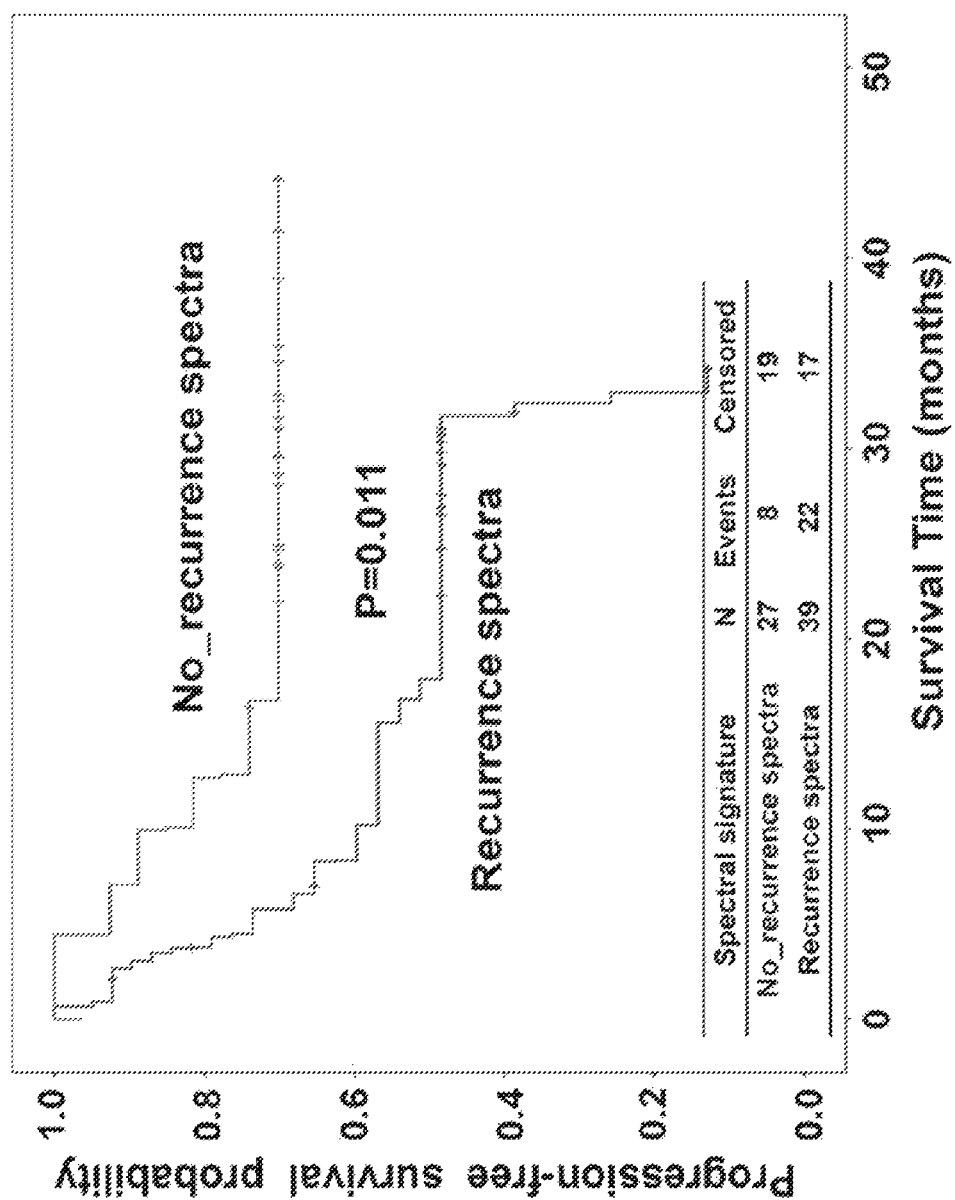

Under multivariate analysis, patients with poor survival spectra showed a trend of correlation with increased risk of death compared to patients with non-poor survival spectra (Cox regression model, HR [95% CI]=2.48 (0.81-7.57), P=0.111, Table 3). Meanwhile, patients with recurrence spectra had a statistically significant, 2.78 fold higher relative risk of disease recurrence (Cox regression model, HR [95% CI]=2.78 (1.10-7.00), P=0.030, Table 3). The Kaplan-Meier method also demonstrated that differences in overall survival (OS) and progression-free survival (PFS) showed corresponding differences in spectral signature. Patients with poor survival spectra exhibited significantly shorter overall survival compared to those with non-poor survival spectra (log-rank P=0.028, FIG. 6A). As expected, those with recurrence spectra were significantly associated with reduced progression-free survival rate compared to those with no-recurrence spectra (log-rank P=0.011, FIG. 6B).

TABLE 3

Association of spectra groups with overall or progression-free survival of esophageal cancer patients under multivariate analysis.

| Variables | N | HR (95% CI) | *P value |
|---|---|---|---|
| Non-poor_survival spectra | 43 | 1 | 0.111 |
| Poor_survival spectra | 23 | 2.48 (0.81-7.57) | |
| Progression-free Survival | | | |
| No_recurrence spectra | 27 | 1 | 0.030 |
| Recurrence spectra | 39 | 2.78 (1.10-7.00) | |

*Adjusted for T_stage, N_stage, site, CCRT treatment and cell type.

As described above, some of current technologies provide detailed information about global changes in gene expression for therapeutic strategies assessment; however, they are not designed for real-time in-situ assessment and require considerable time and cost. Absorption spectroscopy is a potentially powerful tool for cancer diagnosis due to its ability to provide accurate integral absorption information about the sample in real-time or in-situ.

Visible light is safe and easy to work with for clinical diagnosis. The visible absorption spectral signatures in esophageal normal and tumor tissues is distinct enough to provide valuable diagnostic information. We demonstrated the discrimination of the spectral signatures in normal and tumor tissues; and the tissues from patients with different clinical outcomes, including CCRT response, survival and recurrence (FIGS. 2 and 3).

One skilled in the art may concerns that absorption microscopy in the transmission mode cannot be applied reliably for in-situ cancer diagnosis because it is not possible to effectively detect light penetrated through the human body. In fact, the TDAS was designed to be able to measure an absorption spectrum in both the transmission and reflection modes (FIG. 1). We established a prediction model by using the data we collected in the transmission mode because of their higher signal-to-noise ratio compared to the data we collected in the reflection mode. Our results revealed that the absorption spectra measured in the reflection mode were almost identical to those measured in the transmission mode.

By the embodiments described above, the present invention demonstrates the visible-absorption spectroscopy as a tool for evaluating CCRT response and as a prognostic biomarker of esophageal cancer. Further, the CCRT response prediction result achieves the sensitivity of 75% and specificity of 73.3%; the survival prediction rate achieves the sensitivity of 100%.

What is claimed is:

1. An optical method for predicting treatment response of a esophageal cancer patient, comprising:
    collecting a tumor tissue sample from the esophageal cancer patient;
    subjecting the tumor tissue sample to spectral analysis via a two dimensional absorption spectrum measurement system (TDAS) to obtain an optical absorption spectrum of the tumor tissue sample, wherein the optical absorption spectrum of the tumor tissue sample is a visible optical absorption spectrum;
    normalizing and incorporating the optical absorption spectrum of the tumor tissue sample, into a database, wherein the database stores a plurality of spectral data grouped by a principal component analysis, a plural of spectral variables of principal component analysis is obtained from wavelength of 450-475 nm and 625-650 nm, and first eight principal components (PCs) describe a majority of spectral variables for the plurality of spectral data stored in the database; and
    grouping the optical absorption spectrum of the tumor tissue sample from the esophageal cancer patient by PC_7 and PC_2 values of the principal component analysis to determine whether the esophageal cancer patient is identified as having good response or poor response to the treatment;
    wherein the PC_7 and PC_2 values are used to differentiate poor responders and good responders with a sensitivity of 75% and a specificity of 73.3%; and
    wherein the treatment is concurrent chemoradiotherapy.

2. The optical method according to claim 1, wherein the optical absorption spectrum of the tumor tissue sample is an optical absorption spectrum captured by a wavelength from 450 to 650 nm.

3. The optical method according to claim 1, wherein the optical absorption spectrum of the tumor tissue sample is a transmission absorption spectrum.

4. The optical method according to claim 1, wherein the database is pre-stored an effective amount of normalized optical absorption spectra of tumor tissue samples.

5. An optical method for predicting survival of esophageal cancer patients, comprising:
   collecting a tumor tissue sample from an esophageal cancer patient;
   subjecting the tumor tissue sample to spectral analysis via a two dimensional absorption spectrum measurement system (TDAS) to obtain an optical absorption spectrum of the tumor tissue sample, wherein the optical absorption spectrum of the tumor tissue sample is a visible optical absorption spectrum;
   normalizing and incorporating the optical absorption spectrum of the tumor tissue sample into a database, wherein the database stores a plurality of spectral data grouped by a principal component analysis, a plural of spectral variables of principal component analysis is obtained from wavelength of 450-475 nm and 625-650 nm, and first eight principal components (PCs) describe a majority of spectral variables for the plurality of spectral data stored in the database; and
   grouping the optical absorption spectrum of the tumor tissue sample from the esophageal cancer patient by PC_1 and PC_3 values of the principal component analysis to determine the esophageal cancer patient is identified as poor survival or non-poor survival.

6. The optical method according to claim 5, wherein the poor survival defined as the esophageal cancer patient is alive within 1 year, and the non-poor survival defined as the esophageal cancer patient is alive over 1 year.

7. The optical method according to claim 5, wherein the optical absorption spectrum of the tumor tissue sample is an optical absorption spectrum captured by a wavelength from 450 to 650 nm.

8. The optical method according to claim 6, wherein the optical absorption spectrum of the tumor tissue sample is an optical absorption spectrum captured by a wavelength from 450 to 650 nm.

9. The optical method according to claim 5, wherein the optical absorption spectrum of the tumor tissue sample is a transmission absorption spectrum.

10. The optical method according to claim 6, wherein the optical absorption spectrum of the tumor tissue sample is a transmission absorption spectrum.

11. The optical method according to claim 5, wherein the database is pre-stored an effective amount of normalized optical absorption spectra of tumor tissue samples.

12. The optical method according to claim 6, wherein the database is pre-stored an effective amount of normalized optical absorption spectra of tumor tissue samples.

13. An optical method for predicting recurrence of esophageal cancer patients, comprising:
   collecting a tumor tissue sample from an esophageal cancer patient;
   subjecting the tumor tissue sample to spectral analysis via a two dimensional absorption spectrum measurement system (TDAS) to obtain an optical absorption spectrum of the tumor tissue sample, wherein the optical absorption spectrum of the tumor tissue sample is a visible optical absorption spectrum;
   normalizing and incorporating the optical absorption spectrum of the tumor tissue sample, into a database, wherein the database stores a plurality of spectral data grouped by a principal component analysis, a plural of spectral variables of principal component analysis is obtained from wavelength of 450-475 nm and 625-650 nm, and first eight principal components (PCs) describe a majority of spectral variables for the plurality of spectral data stored in the database; and
   grouping the optical absorption spectrum of the tumor tissue sample from the esophageal cancer patient by PC_6 and PC_5 values of principal component analysis to determine the esophageal cancer patient is identified as recurrence or no recurrence.

14. The optical method according to claim 13, wherein the recurrence defined as the esophageal cancer patient experience tumor recurrence or die within 6 months and the no recurrence defined as the esophageal cancer patient wouldn't experience tumor recurrence within 6 months.

15. The optical method according to claim 13, wherein the optical absorption spectrum of the tumor tissue sample is an optical absorption spectrum captured by a wavelength from 450 to 650 nm.

16. The optical method according to claim 14, wherein the optical absorption spectrum of the tumor tissue sample is an optical absorption spectrum captured by a wavelength from 450 to 650 nm.

17. The optical method according to claim 13, wherein the optical absorption spectrum of the tumor tissue sample is a transmission absorption spectrum.

18. The optical method according to claim 14, wherein the optical absorption spectrum of the tumor tissue sample is a transmission absorption spectrum.

19. The optical method according to claim 13, wherein the database is pre-stored an effective amount of normalized optical absorption spectra of tumor tissue samples.

20. The optical method according to claim 14, wherein the database is pre-stored an effective amount of normalized optical absorption spectra of tumor tissue samples.

* * * * *